US006995260B2

(12) United States Patent
Wu et al.

(10) Patent No.: US 6,995,260 B2
(45) Date of Patent: Feb. 7, 2006

(54) CARBORANYLPORPHYRINS AND USES THEREOF

(75) Inventors: Haitao Wu, Wading River, NY (US); Michiko Miura, Hampton Bay, NY (US)

(73) Assignee: Brookhaven Science Associates, LLC, Upton, NY (US)

(*) Notice: Subject to any disclaimer, the term of this patent is extended or adjusted under 35 U.S.C. 154(b) by 88 days.

(21) Appl. No.: 10/848,741

(22) Filed: May 20, 2004

(65) Prior Publication Data

US 2005/0260128 A1    Nov. 24, 2005

(51) Int. Cl.
*C07B 47/00* (2006.01)
*A61B 5/055* (2006.01)
*A61B 10/00* (2006.01)
*C07F 5/10* (2006.01)
*A61K 31/555* (2006.01)

(52) U.S. Cl. .................... 540/145; 534/15; 514/185; 514/410; 424/9.1; 424/9.362; 424/9.61

(58) Field of Classification Search ............... 540/145; 534/15; 514/185, 410; 424/9.1, 9.362, 9.61
See application file for complete search history.

(56) References Cited

U.S. PATENT DOCUMENTS

| | | | |
|---|---|---|---|
| 4,783,529 A | 11/1988 | Lavallee et al. | |
| 4,959,356 A | 9/1990 | Miura et al. | |
| 5,149,801 A | 9/1992 | Kahl et al. | |
| 5,162,231 A | 11/1992 | Cole et al. | |
| 5,268,371 A | 12/1993 | Mauclaire et al. | |
| 5,312,896 A | 5/1994 | Bhardwaj et al. | |
| 5,563,132 A | 10/1996 | Bodaness | |
| 5,648,485 A * | 7/1997 | Dolphin et al. | 540/474 |
| 5,654,423 A | 8/1997 | Kahl et al. | |
| 5,674,467 A | 10/1997 | Maier et al. | |
| 5,877,165 A * | 3/1999 | Miura et al. | 514/64 |
| 5,955,586 A | 9/1999 | Sessler et al. | |
| 6,010,805 A | 1/2000 | Scanlon, Jr. et al. | |
| 6,066,628 A | 5/2000 | Stojiljkovic et al. | |
| 6,566,517 B2 | 5/2003 | Miura et al. | |
| 2004/0023942 A1 * | 2/2004 | Bart et al. | 514/185 |

FOREIGN PATENT DOCUMENTS

WO    WO 01/85736 A1    11/2001
WO    WO 2004030661 A2 *    4/2004

OTHER PUBLICATIONS

Frixa et al. (Org. Biomol. Chem., 2003, 1, 306-317.)*
Foye et al. (Principles of Medicinal Chemistry, Fourth Edition., Williams & Wilkins 1995. pp. 902-907).*
Frixa et al. Synthesis of meso-substituted porphyrins carrying carboranes and oligo(ethylene glycol) units for potential applications in boron neutron capture therapy.Org. Biomol. Chem., 2003, 1, 306-317.*

Morris et al., "Porphyrin-mediated boron neutron capture therapy: evaluation of the reactions of skin and central nervous system," *Int. J. Radiat. Biol.,* 79(3): 149-158 (2003).
Vincente, et al., "Synthesis, dark toxicity and induction of in vitro DNA photodamage by a tetra (4-*nido*-carboranylphenyl)prophyrin," *J. Photochem. Photobiol. B. Biology,* 68(2-3): 123-132 (2002).
Maderna et al., "Synthesis of a porphyrin-labelled carboranyl phosphate diester: a potential new drug for boron neutron capture therapy of cancer," *Chem. Commun.,* 16: 1784-1785 (2002).
Miura et al., "Boron Neutron Capture of a Murine Mammary Carcinoma using a Lipophilic Carboranyltetraphenylporphyrin," *Radiat. Res.,* 155(4): 603-610 (2001).
Miura et al., "Evaluation of carborane-containing porphyrins as tumor targeting agents for boron neutron capture therapy," *Br. J. Radiol.,* 71(847): 773-781 (1998).
Miura et al., "Synthesis of a Nickel Tetracarboranylphenylporphyrin for Boron Neutro-Capture Therapy: Biodistribution and Toxicity in Tumor-Bearing Mice," *Int. J. Cancer,* 68(1): 114-119 (1996).
Kahl et al., "A Carboranyl Porphyrin for Boron Neutron Capture Therapy of Brain Tumors," *Basic Life Sci.,* 50: 193-203 (1989).
Miura et al., "Biodistribution of copper carboranyltetraphenylporphyrins in rodents bearing an isogeneic or human neoplasm," *J. NeuroOncol,* 5: 111-117 (2001).
Berlin et al., "Are Porphyrin Mixtures Favorable Photodynamic Anticancer Drugs? A Model Study with Combinatorial Libraries of Tetraphenylporphyrins," *Combinatorial Chemistry,* 61(2): 107-118 (1998).
Miller et al., "In Vivo Animal Studies with Gadolinium (III) Texaphyrin As a Radiation Enhancer," *Int. J. Radiat. Oncol. Biol. Phys.,* 45(4): 981-989 (1999).
Bhyrappa et al., "Octabromotetraphenylporphyrin and Its Metal Derivatives: Electronic Structure and Electrochemical Properties," *Inorg. Chem.,* 30: 239-245 (1991).

(Continued)

*Primary Examiner*—James O. Wilson
*Assistant Examiner*—Matthew L. Fedowitz
(74) *Attorney, Agent, or Firm*—Margaret C. Bogosian

(57) ABSTRACT

The present invention is directed to low toxicity boronated compounds and methods for their use in the treatment, visualization, and diagnosis of tumors. More specifically, the present invention is directed to low toxicity carborane-containing 5, 10, 15, 20-tetraphenylporphyrin compounds and methods for their use particularly in boron neutron capture therapy (BNCT) and photodynamic therapy (PDT) for the treatment of tumors of the brain, head and neck, and surrounding tissue. The invention is also directed to using these carborane-containing tetraphenyl porphyrin compounds to methods of tumor imaging and/or diagnosis such as MRI, SPECT, or PET.

30 Claims, No Drawings

OTHER PUBLICATIONS

Birnbaum et al., "$^{19}$F NMR Spectra and Structures of Halogenated Porphyrins," *Inorg. Chem.,* 34(14): 3625-3632 (1995).

Fairchild et al., "Current Status of $^{10}$B-Neutron Capture Therapy: Enhancement of Tumor Dose Via Beam Filtration and Dose Rate, and the Effects of These Parameters on Minimum Boron Content: a Theoretical Evaluation," *Int. J. Radiat. Oncol. Biol. Phys.,* 11(4): 831-840 (1985).

Woller et al., "2, 3, 7, 8, 12, 13, 17, 18-Octafluoro-5, 10, 15, 20-tetraarylporphyrins and Their Zinc Complexes: First Spectroscopic, Electrochemical, and Structural Characterization of a Perfluorinated Tetraarylmetalloporphyrin," *J. Org. Chem.,* 62(6): 1588-1593 (1997).

Woller et al., "A Straightforward Synthesis of 3,4-Difluoropyrrole," *J. Org. Chem.,* 63(16): 5706-5707 (1998).

Ozette et al., "New Metalloporphyrins with Extremely Altered Redox Properties: Synthesis, Structure, and Facile Reduction to Air-Stable n-Anion Radicals of Zinc and Nickel β-Heptanitroporphyrins," *J. Am. Chem. Soc.,* 119 (27): 6442-6443 (1997).

Chanana et al., "Boron Neutron Capture Therapy for Glioblastoma Multiforme: Interim Results from the Phase I/II Dose-Escalation Studies," *Neurosurgery,* 44(6): 1182-1193 (1999).

Vincente et al., "Syntheses of carbon—carbon linked carboranylated porphyrins for boron neutron capture therapy of cancer." *Tetrahedron Letters,* 41: 7623-7627 (2000).

Evstigneeva, "Synthesis of Carboranylporphyrins and the Perspectives of Their Use for Boron Neutron Capture Therapy," *Molecules,* 5: 1479-80 (2001).

Zakharkin et al., "Synthesis of carboranyl derivatives of deuteroporphyrin IX, " *Russian Chemical Bulletin,* 48(12): 2312-14 (1999).

"Brain Tumor Patients Offered New Hope with Expanded Trial of Promising Therapy," Press Release, Brookhaven National Labs, Nov. 1998, <http://virtualtrials.com/bnct2.cfm.>.

Gomez, "Boron Neutron Capture Therapy (BNCT)," Dec. 1, 1998, Lawrence Berkeley National Laboratory, <http://www.virtualtrials.com/bnct.cfm>.

* cited by examiner

CARBORANYLPORPHYRINS AND USES THEREOF

This invention was made with Government support under contract number DE-AC02-098CH10886, awarded by the U.S. Department of Energy. The Government has certain rights in the invention.

BACKGROUND OF THE INVENTION

The efficacy of radiation and chemical methods in the treatment of cancers has been limited by a lack of selective targeting of tumor cells by the therapeutic agent. In an effort to spare normal tissue, current tumor treatment methods have therefore restricted radiation and/or chemical treatment doses to levels that are well below optimal or clinically adequate. Thus, designing compounds that are capable, either alone or as part of a therapeutic method, of selectively targeting and destroying tumor cells, is a field of intense study.

Because of the known affinity of porphyrins to neoplastic tissues, there has been intense interest in using porphyrins as delivery agents in the treatment of neoplasms in the brain, head and neck, and related tumors. Porphyrins in general belong to a class of colored, aromatic tetrapyrrole compounds, some of which are found naturally in plants and animals, e.g., chlorophyll and heme, respectively.

Porphyrins and other tetrapyrroles with relatively long singlet lifetimes have already been used to treat malignant tumors using photodynamic therapy (PDT). In PDT, the patient is first injected with a photosensitizing drug, typically a porphyrin. The tumor cells, now photosensitized, are susceptible to destruction when exposed to an intense beam of laser red light. The biochemical mechanism of cell damage in PDT is believed to be mediated largely by singlet oxygen, which is produced by transfer of energy from the light-excited porphyrin molecule to an oxygen molecule. However, PDT has been limited predominantly by the photosensitizing compounds, which have lower than adequate selectivity to tumor cells and higher than optimal toxicity to normal tissue.

A promising new form of cancer therapy is boron neutron-capture therapy (BNCT). BNCT is a bimodal cancer treatment based on the selective accumulation of a stable nuclide of boron known as boron-10, or $^{10}B$, in the tumor, followed by irradiation of the tumor with thermalized neutrons. The thermalized neutrons impinge on the boron-10, causing nuclear fission (decay reaction). The nuclear fission reaction causes the highly localized release of vast amounts of energy in the form of high linear-energy-transfer (LET) radiation, which can kill cells more efficiently (higher relative biological effect) than low LET radiation, such as x-rays.

In BNCT, the boron-containing compound must be non-toxic or of low toxicity when administered in therapeutically effective amounts, as well as being capable of selectively accumulating in cancerous tissue. For example, clinical BNCT for malignant brain tumors was carried out at the Brookhaven National Laboratory Medical Department using p-boronophenylalanine (BPA) as the boron carrier (Chanana et al., *Neurosurgery*, 44, 1182–1192, 1999). Although BPA has the advantage of low chemical toxicity, it accumulates in critical normal tissues at levels that are less than desirable. In particular, the tumor-to-normal brain and tumor-to-blood boron concentrations are in the ratio of approximately 3:1. Such low specificity limits the maximum dose of BPA to a tumor since the allowable dose to normal tissue will be the limiting factor.

A particular class of synthetic porphyrins, known as tetraphenyl porphyrins, have garnered intense interest in the design of new boron carrier compounds for BNCT. Tetraphenylporphyrins (TPPs) contain four phenyl groups, typically on the 5, 10, 15, and 20 positions of the porphyrin ring. An advantage of TPPs is their ease of synthesis.

The solubility of TPPs can be controlled by the substituents, generally on the phenyl positions. Those TPPs containing sulfonates or carboxylates are water-soluble. However, some of the carborane-containing TPPs have high lipophilic properties, which can require high amounts of non-aqueous excipients before administration into animals. High amounts of excipients may reduce the biological effect of the porphyrin by, for example, changing the microlocalization within the tumor cell such that it may be bound to membranes instead of homogeneously distributed throughout the cell. In addition, the use of more hydrophilic bonds such as amide, ester, or urea bonds, although significantly more hydrophilic than carbon—carbon linkages, are known to hydrolyze under numerous types of conditions. Such hydrolysis is particularly problematic when such hydrophilic bonds are employed to attach the carboranyl group to the porphyrin molecule, since hydrolysis results in loss of the carbonyl group before reaching the target.

Therefore, there continues to be an effort to reduce the lipophilic behavior of TPPs while not compromising their chemical stability. For example, international Patent Application No. WO 01/85736 by Vicente et al describes the synthesis and use of tetraphenylporphyrin compounds that contain hydrophilic groups. A salient feature of the Vicente compounds is the attachment of the carboranyl group to the phenyl group by, exclusively, a carbon—carbon linkage. Though such a carbon—carbon linkage is not prone to hydrolysis or other chemical attack, such a linkage is significantly hydrophobic.

Porphyrins also have the advantage of having the ability to chelate metal ions in its interior. Such chelated porphyrins can additionally function as visualization tools for real-time monitoring of porphyrin concentration and/or diagnostic agents. For example, when chelated to paramagnetic metal ions, porphyrins may function as contrast agents in magnetic resonance imaging (MRI), and when chelated to radioactive metal ions, porphyrins may function as imaging agents for single photon emission computed tomography (SPECT) or positron emission tomography (PET).

In addition, by using chelated boron-containing porphyrins in BNCT, boron concentration and distribution in and around the tumor and all tissues within the irradiated treatment volume can be accurately and rapidly determined noninvasively before and during the irradiation. Such diagnostic information allows BNCT treatment to be performed more quickly, accurately, and safely, by lowering exposures of epithermal neutrons in regions of tissues known to contain high levels of boron. Short irradiations would obviate the inconvenience and discomfort to the patient of long and often awkward positioning of the head at a reactor port. However, the anticipated use of accelerator-generated neutrons would likely produce a significantly lower flux and hence effect longer irradiation times, so that compounds that have longer tumor retention times would become critical.

Accordingly, there is a need for new compounds, especially boron-containing porphyrins, with long retention times in tumors, and that selectively target and destroy tumor cells with minimal damage to normal tissue. In addition, there is a need for more effective methods for the treatment of brain, head and neck, and related tumors, and more particularly, more effective BNCT treatments and boron-delivery compounds used therein.

SUMMARY OF THE INVENTION

The present invention is directed to low toxicity boronated compounds and methods for their use in the treatment, visualization, and diagnosis of tumors. More specifically, the present invention is directed to low toxicity boronated 5, 10, 15, 20-tetraphenylporphyrin compounds and methods for their use particularly in boron neutron capture therapy (BNCT) or photodynamic therapy (PDT) for the treatment of tumors of the brain, head and neck, and surrounding tissue.

In particular, the present invention is directed to boron-containing 5, 10, 15, 20-tetraphenylporphyrins of the formula

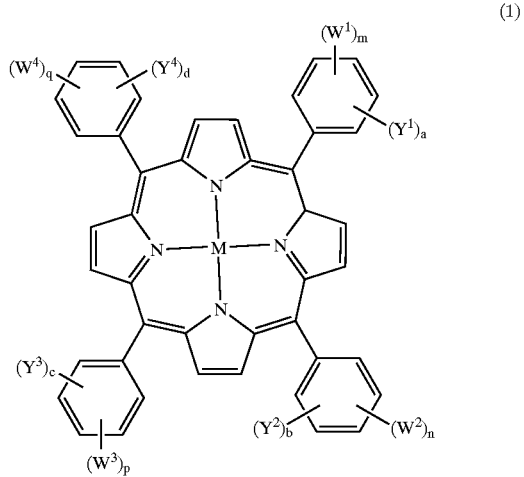

(1)

wherein:

$Y^1$, $Y^2$, $Y^3$, and $Y^4$, are independently on the ortho, meta or para position on the phenyl rings, and are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by the following formula:

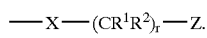

(2)

provided that at least one of $Y^1$, $Y^2$, $Y^3$, and $Y^4$ represents formula (2);

X is oxygen or sulfur;

$R^1$, $R^2$, $R^5$, $R^6$, $R^7$, $R^8$, and $R^9$ are independently selected from hydrogen and $C_1$ to $C_4$ alkyl;

Z is a carborane cluster comprising at least two carbon atoms and at least three boron atoms, or at least one carbon atom and at least five boron atoms, within a cage structure;

r is 0 or an integer from 1 to 20;

$W^1$, $W^2$, $W^3$, and $W^4$ are hydrophilic groups independently selected from hydroxy, alkoxy, —C(O)OR$^5$, —SOR$^6$, —SO$_2$R$^6$, nitro, amido, ureido, carbamato, —SR$^7$, —NR$^8$R$^9$, or polyalkylene oxide;

a, b, c, and d independently represent an integer from 1 to 4;

m, n, p, and q are independently 0 or an integer from 1 to 4;

provided that at least one of m, n, p, and q is not zero, and each of the sums a+m, b+n, c+p, and d+q, independently represents an integer from 1 to 5; and M is either two hydrogen ions; a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein the porphyrin-metal complex derived from a single monovalent metal ion is charge-balanced by a counter cation, and the porphyrin-metal complex derived from a trivalent, tetravalent, pentavalent, hexavalent metal ion is charge-balanced by an appropriate number of counter anions, dianions, or trianions.

Z is preferably selected from the carboranes —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho, meta-, or para-carborane.

M is preferably vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), or gadolinium (Gd). In a more preferred embodiment, M is copper (Cu) or nickel (Ni).

In a preferred embodiment, a, b, c, and d are 1, and $Y^1$, $Y^2$, $Y^3$, and $Y^4$ are represented by

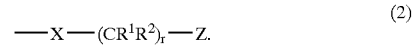

(2)

In a further preferred embodiment, X is O; $R^1$ and $R^2$ are H; r is 1; and m, n, p and q are each 1.

In one embodiment, $Y^1$, $Y^2$, $Y^3$, and $Y^4$ are in the para position on the phenyl ring, and $W^1$, $W^2$, $W^3$, and $W^4$ are independently, hydroxy or alkoxy groups. More preferably, the hydroxy or alkoxy groups are in the meta position of the phenyl ring.

Preferably, $W^1$, $W^2$, $W^3$, and $W^4$ are methoxy groups. More preferably, the methoxy groups are in the meta position of the phenyl ring.

In another embodiment, $Y^1$, $Y^2$, $Y^3$, and $Y^4$ are represented by

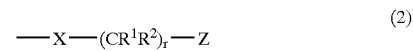

(2)

and are in the para position on the phenyl ring; X is O; $R^1$ and $R^2$ are H; r is 1; m, n, p and q are each 1, and $W^1$, $W^2$, $W^3$, and $W^4$ are hydroxy. In yet another embodiment, when the porphyrin compound requires a counter dianion, the counter dianion is a porphyrin compound containing a divalent negative charge. The porphyrin compound containing a divalent negative charge may be a carborane-containing porphyrin compound of the present invention, with the proviso that M is absent.

The present invention also includes methods of tumor imaging by SPECT, PET, or MRI, as well as methods of bimodal cancer treatment such as BNCT and PDT that require the administration to a subject of a composition that comprises one or more of the porphyrin compounds described above. In a preferred embodiment, the composition is essentially one or more of the porphyrin compounds described above.

DETAILED DESCRIPTION OF THE INVENTION

The invention relates to boron-containing 5, 10, 15, 20-tetraphenyl porphyrins having the formula

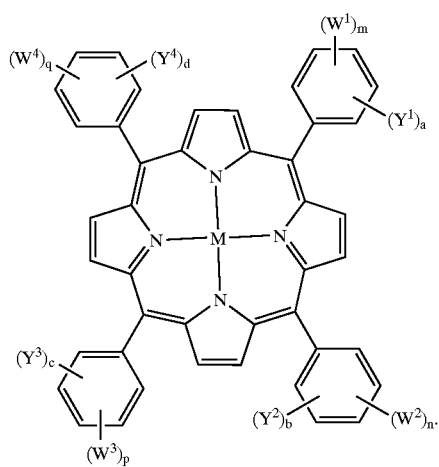

(1)

$Y^1$, $Y^2$, $Y^3$, and $Y^4$, are independently on the ortho, meta or para position on the phenyl rings. $Y^1$, $Y^2$ $Y^3$, and $Y^4$ are independently hydrogen, alkyl, cycloalkyl, aryl, alkylaryl, arylalkyl, heteroaryl, or a substituent represented by

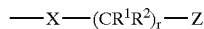

When any of $Y^1$, $Y^2$, $Y^3$, or $Y^4$ is alkyl, alkyl is a straight chain or branched alkyl group containing 1 to 20 carbon atoms including, optionally, up to three double or triple bonds. Some examples of alkyl groups include methyl, ethyl, n-propyl, iso-propyl, n-butyl, iso-butyl, sec-butyl, tert-butyl, propenyl, 2-butenyl, 3-butenyl, 3-butynyl, 2-methyl-2-butenyl, n-pentyl, dodecyl, hexadecyl, octadecyl, and eicosyl.

The alkyl group may be unsubstituted or substituted with 1 to 4 hydrophilic groups. Some examples of suitable hydrophilic groups include hydroxy, alkoxy, —C(O)OR$^5$, —SOR$^6$, —SO$_2$R$^6$, nitro, amido, ureido, carbamato, —SR$^7$, —NR$^8$R$^9$, and poly-alkyleneoxide. R$^5$, R$^6$, R$^7$, R$^8$, and R$^9$ are independently selected from hydrogen and alkyl groups as defined above, except that the alkyl groups for R$^5$, R$^6$, R$^7$, R$^8$, and R$^9$ contain 1 to 4 carbon atoms.

The carbon atoms of the alkyl group may also be substituted with 1 to 4 heteroatoms. In this specification, heteroatoms are O, N, or S. The heteroatoms are not adjacent, and are separated by at least one carbon atom.

When any of $Y^1$, $Y^2$, $Y^3$, or $Y^4$ is cycloalkyl, the cycloalkyl ring is a 4, 5, 6, or 7 member cycloalkyl ring. The ring may be saturated, or may contain 1 to 4 unsaturated (i.e., double or triple) bonds. Some examples of saturated cycloalkyl rings include cyclobutane, cyclopentane, cyclohexane, and cyclopentane rings. Some examples of unsaturated cycloalkyl rings include cyclobutene, cyclopentene, cyclohexene, and 1,3-cycloheptadiene rings.

The cycloalkyl ring may optionally be substituted with 1 to 4 heteroatoms of O, N, or S. Some examples of cycloalkyl rings substituted with heteroatoms include pyrrolidine, piperidine, piperazine, tetrahydrofuran, furan, thiophene, 1,3-oxazolidine, imidazole, and pyrrole rings. The cycloalkyl rings may be optionally substituted with alkyl as defined above, or with 1 to 4 hydrophilic groups, also as defined above.

The cycloalkyl ring may be fused to 1 to 3 additional 4, 5, 6, or 7 member cycloalkyl or phenyl rings. Some examples of fused cycloalkyl rings are bicyclo[3.3.0]octane, bicyclo[4.3.0]non-3-ene, triphenylene, and 1,2,3,4-tetrahydronaphthalene rings.

When any of $Y^1$, $Y^2$, $Y^3$, or $Y^4$ is aryl, aryl is a 5, 6, or 7 member aromatic ring, preferably a phenyl ring. The aryl rings may be optionally substituted with alkyl as defined above to produce alkylaryl or arylalkyl groups. The aryl, alkylaryl, and arylalkyl groups may be substituted with 1 to 4 hydrophilic groups, as defined above.

The aryl ring may optionally be substituted with 1 to 4 heteroatoms of O, N, or S, resulting in a heteroaryl ring. Some examples of heteroaryl rings include thiophene, pyridine, oxazole, thiazole, oxazine, and pyrazine rings. The heteroaryl ring may be substituted with 1 to 4 hydrophilic groups, as defined above.

The aryl or heteroaryl ring may also be fused to 1 to 3 additional 5, 6, or 7 member aryl or heteroaryl rings. Some examples of fused aryl and heteroaryl rings include naphthalene, anthracene, phenanthrene, triphenylene, chrysene, indoline, quinoline, and tetraazanaphthalene (pteridine) rings.

At least one of $Y^1$, $Y^2$, $Y^3$, or $Y^4$ is represented by the formula

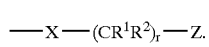

(2)

In formula (2), X is oxygen or sulfur, and R$^1$ and R$^2$ are independently selected from hydrogen and alkyl groups as defined above, except that the alkyl groups for R$^1$ and R$^2$ contain 1 to 4 carbon atoms. The subscript r is 0 or an integer from 1 to 20.

Z is a carborane cluster comprising at least two carbon atoms and at least three boron atoms, or at least one carbon atom and at least five boron atoms, within a cage structure. Some examples of carborane clusters include the regular polyhedral carborane clusters, also known as closo structures, as well as ionized fragments of the polyhedral clusters, also known as nido structures. Some examples of the preferred carboranes of the present invention include —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

W$^1$, W$^2$, W$^3$, and W$^4$ are hydrophilic groups independently selected from hydroxy, alkoxy, —C(O)OR$^5$, —SOR$^6$, —SO$_2$R$^6$, nitro, amido, ureido, carbamato, —SR$^7$, —NR$^8$R$^9$, or polyalkylene oxide, wherein R$^5$, R$^6$, R$^7$, R$^8$, and R$^9$ have been previously defined.

In this specification, an alkoxy group contains an alkyl portion as defined above. Some examples of alkoxy groups include methoxy, ethoxy, propoxy, n-butoxy, t-butoxy, and dodecyloxy.

A polyalkylene oxide is defined according to the formula —(CH$_2$)$_d$—O—[(CH$_2$)$_e$—O—]$_x$—[(CH$_2$)$_f$—O—]$_y$—(CH$_2$)$_g$—OR', wherein, independently, d is 0, or an integer from 1 to 10, e is 0, or an integer from 1 to 10, f is 1 to 10, g is 1 to 10, x and y are each independently 1 or 0, and R' is either H or an alkyl group as defined previously, provided that when e is 0, then x is 0; when f is 0, then y is 0; when e is not 0, then x is 1; and when f is not 0, then y is 1.

A preferable polyalkylene oxide of the invention is polyethylene oxide. Polyethylene oxide is defined according to the formula $-(CH_2)_d-O-[(CH_2)_e-O-]_x-[(CH_2)_f-O-]_y-(CH_2)_g-OR'$, wherein, independently, d is 0 or 2, e is 0 or 2, f is 0 or 2, g is 2, x and y are each independently 1 or 0, and R' is either H or an ethyl group, provided that when e is 0, then x is 0; when f is 0, then y is 0; when e is not 0, then x is 1; and when f is not 0, then y is 1.

The subscripts m, n, p, and q are independently 0 or an integer from 1 to 4, provided that at least one of m, n, p, and q is not zero; and the subscripts a, b, c, and d independently represent an integer from 1 to 4; provided that at least one of m, n, p, and q is not zero, and each of the sums a+m, b+n, c+p, and d+q, independently represents an integer from 1 to 5.

In formula (1), M may be two hydrogen ions, a single monovalent metal ion, or two monovalent metal ions. Some examples of suitable monovalent metal ions include $Li^{+1}$, $Na^{+1}$, $K^{+1}$, $Cu^{+1}$, $Ag^{+1}$, $Au^{+1}$, and $Tl^{+1}$. When M is a single monovalent metal ion, the resulting porphyrin-metal complex anion is charge-balanced by a counter cation. Some examples of counter cations include any of the foregoing monovalent metal ions, and ammonium and phosphonium cations, such as tetramethylammonium, tetrabutylammonium, and tetraphenylammonium. The counter cation may be either bound or associated in some form with the porphyrin-metal complex.

M may also be a divalent metal ion. Some examples of suitable divalent metal ions include $V^{+2}$, $Mn^{+2}$, $Fe^{+2}$, $Ru^{+2}$, $Co^{+2}$, $Ni^{+2}$, $Cu^{+2}$, $Pd^{+2}$, $Pt^{+2}$, $Zn^{+2}$, $Ca^{+2}$, $Mg^{+2}$, $Sr^{+2}$, and $Ba^{+2}$.

Alternatively, M may be a trivalent, tetravalent, pentavalent, or hexavalent metal ion. Some examples of suitable trivalent metal ions include $Gd^{+3}$, $Y^{+3}$, $In^{+3}$, $Cr^{+3}$, $Ga^{+3}$, $Al^{+3}$, $Eu^{+3}$, and $Dy^{+3}$. Some examples of suitable tetravalent metal ions include $Tc^{+4}$, $Ge^{+4}$, $Sn^{+4}$, and $Pt^{+4}$. An example of a suitable pentavalent metal ion is $Tc^{+5}$. Some examples of suitable hexavalent metal ions include $W^{+6}$, $Tc^{+6}$, and $Mo^{+6}$. The resulting porphyrin-metal complex cation is charge-balanced by an appropriate number of counter anions, dianions, or trianions. For example, a porphyrin-metal complex cation derived from a trivalent metal ion may be charge-balanced by a single counter anion, and such a complex derived from a tetravalent metal ion may, for example, be charge-balanced by a single counter dianion or two counter anions, and so on.

Some examples of suitable counter anions include chloride, perchlorate, sulfate, nitrate, and tetrafluoroborate. Some examples of suitable counter dianions include oxide, sulfide, or a porphyrin compound containing a divalent negative charge. The porphyrin compound containing a divalent negative charge may be a porphyrin compound of the present invention with the proviso that M is absent. An example of a suitable counter trianion includes phosphate.

The counter anion, dianion, or trianion may be either bound or associated in some form with a carborane-containing porphyrin compound of the present invention. The carborane-containing porphyrin compound may also be bound to or associated with neutrally charged molecules, such as molecules of solvation, for example, water, acetonitrile, methanol, and so on.

In addition, M may be a radioactive metal ion imageable by single photon emission computed tomography (SPECT) or positron emission tomography (PET). Some examples of radioactive metals suitable for SPECT are $^{67}Cu$, $^{99m}Tc$, $^{111}In$, and those for PET include $^{64}Cu$, $^{55}Co$. M may also be a radioactive metal useful as a radiopharmaceutical for therapy. Some examples of radioactive metals suitable for such therapy include $^{90}Y$, $^{188}Re$, $^{67}Cu$.

M may also be a paramagnetic metal ion detectable by magnetic resonance imaging (MRI). Some examples of such metals include Mn, Fe, Co, and Gd.

In addition, M may be a metal ion suitable for boron neutron capture therapy (BNCT) or photodynamic therapy (PDT); or a combination thereof. The metal ions suitable for BNCT include those described thus far, with the exclusion of those that are photoactive, such as Zn and Sn. Such photoactive metals, and particularly those with long-lived triplet states, are preferable for PDT. Since the dosage for BNCT is 100 to 1000 times greater than the dosage for PDT, a significant accumulation of photoactive metal in the skin could result if such photoactive metals were used in BNCT. Such an accumulation of photoactive metal may cause biological damage.

The invention also relates to methods of treating tumors. In a preferred embodiment, the method of treating malignant tumors, especially brain tumors, is via BNCT. BNCT is a bimodal cancer treatment based on the selective accumulation of a stable nuclide of boron known as boron-10, or $^{10}B$, in the tumor, followed by irradiation of the tumor with thermalized neutrons. The thermalized neutrons impinge on the boron-10, causing a nuclear fission reaction. The nuclear fission causes the highly localized release of vast amounts of energy in the form of high linear-energy-transfer (LET) radiation, which can more effectively kill cells than low LET radiation, such as x-rays.

Boron-10 undergoes the following nuclear reaction when captured by a thermal neutron:

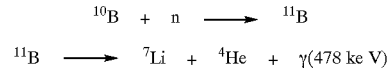

In this nuclear reaction, a boron-10 nucleus captures a neutron forming the metastable nuclide $^{11}B$, which spontaneously and nearly instantaneously disintegrates into a $^4He$ and $^7Li$ particle, which together possess an average total kinetic energy of 2.34 MeV. These two ionized particles travel about 9 μm and 5 μm (7±2 μm) in opposite directions in soft tissue, respectively.

The distances traveled by the $^4He$ and $^7Li$ particles are comparable to the diameter of many tumor and tumor-associated cells. Therefore, the efficacy of BNCT resides in the production of highly localized, high LET ionizing radiation within the tumor. The targeted tumor thus receives a large dose of radiation while sparing surrounding normal tissue.

In the case of brain tumors, after administration of the boron compound, the patient's head is irradiated in the general area of the brain tumor with an incident beam or field of epithermal (0.5 eV–10 keV) neutrons. The neutrons become progressively thermalized (average energy approximately 0.04 eV) as they penetrate deeper into the head. As the neutrons become thermalized, they are more readily captured by the boron-10 concentrated in the tumor cells and/or tumor supporting tissues, since the capture cross section is inversely proportional to the neutron velocity.

In BNCT of malignant brain tumors following the method of the present invention, the patient is first given an infusion of a carborane-containing porphyrin of formula (1), which is highly enriched in boron-10. The carborane-containing porphyrin is then concentrated preferentially in the brain tumor within the effective irradiation volume, which, for brain tumors may be a substantial part of the brain. For example, tumors located in most or all of one hemisphere and some or all of the contralateral hemisphere of the brain can accumulate boronated porphyrins.

The tumor area is then irradiated with thermalized neutrons (primary irradiation), some of which are captured by the boron-10 concentrated in the tumor. The relative probability that the slow-moving thermal neutrons will be captured by the boron-10 nuclide is high compared to the probability of capture by all of the other nuclides normally present in mammalian tissues, provided that boron-10 concentrations in tumor tissues is greater than 30 $\mu$g/g.

Since a minuscule proportion of the boron-10 nuclei in and around a tumor undergoes the nuclear reaction immediately after capturing a neutron, a high concentration of boron-10 in the targeted tissue is necessary for BNCT to be clinically effective. Therefore, to maximize the concentration of boron-10 in the targeted tissue, the carborane clusters are highly enriched in boron-10. Specifically, the boron in the carborane cluster is enriched to at least 95 atom % in boron-10.

An advantage of the present invention over the prior art for the treatment of cancer is that the boron-containing porphyrins of the present invention selectively accumulate in neoplasms in more preferred ratios than other known boron-containing compounds.

Additionally, the porphyrin compounds of the present invention that have been tested in vivo are non-toxic at theoretically therapeutic effective doses. The higher selectivity and lower toxicity of the carborane-containing porphyrins of the present invention allow for the selective destruction of tumor tissue with minimal disruption of normal tissues and tissue function when irradiated.

Another advantage of the carborane-containing porphyrins of the present invention is their increased polarity, imparted through polar groups $W^1$, $W^2$, $W^3$, and $W^4$, on the phenyl rings. The greater polarity of such groups render the tetraphenyl porphyrin compounds less lipophilic, which effects a reduction of the amount of an emulsifying cosolvent during administration. Therefore, the microlocalization within the tumor cell may be improved yielding a higher relative biological effect.

In addition, the ether linkages in the carborane-containing porphyrins of the present invention are more polar than carbon—carbon linkages and therefore, provide a further reduction in lipophilicity. At the same time, the ether linkages possess nearly the same resistance to hydrolysis and other forms of chemical attack as a carbon—carbon linkage.

It is significant that the carborane-containing porphyrins of the present invention may contain in excess of 8 carborane clusters (80 boron atoms). In fact, the present invention includes carborane-containing porphyrin molecules containing 16 carborane clusters, which is higher than any carborane-containing porphyrin currently known. Since such high carborane-containing porphyrin molecules deliver more boron to a target, i.e., are more potent, they permit lower required molar doses of porphyrin as compared to the porphyrin compounds in the prior art. The lower molar dose of carborane-containing porphyrin allows the amount of boron at the target to be significantly increased while keeping blood porphyrin concentrations well below toxic threshold values.

To accumulate the requisite amount of a compound of the present invention in a tumor, generally a systemically injected or infused dose of about 10–50 milligrams of boron-10 per kg body weight in a pharmaceutically acceptable carrier is administered to a patient. The carrier may include such commercially available solvents as Cremophor EL, propylene glycol, Tween 80, polyethylene glycol, or liposomes. The compound is administered in one or more doses, the last dose being given between about 1 hour and one week prior to the epithermal neutron irradiation.

The timing of the neutron exposure depends upon the concentration of the porphyrin in the blood, which decreases more rapidly with time than the porphyrin concentration in the tumor. However, the timing of the administration of the carborane-containing porphyrin depends on various considerations that are well known to those skilled in the art of clinical BNCT, including the pharmacokinetic behavior of the compound, (e.g., the rate of absorption of the compound into the tumor and into the tumor vasculature) and the rate of excretion from and/or metabolism of the compound in the tumor and various other tissues that absorb the compound.

In another preferred embodiment, the method of treating malignant tumors of the present invention is via PDT. PDT is a bimodal cancer treatment based on the selective accumulation of a porphyrin in a tumor, followed by irradiation of the tumor with laser red light. Upon activation with light, an electron of the porphyrin is excited from the singlet ground state to a singlet excited state. The electron then can either return to the singlet ground state with the emission of light causing fluorescence, or it can change its spin via intersystem crossing to the triplet state. In the decay of the triplet back down to the ground state singlet, it can transfer energy to ground state triplet dioxygen which forms the highly reactive singlet oxygen. Biomolecules that react most readily with singlet oxygen include unsaturated lipids and alpha amino-acid residues, both of which are major constituents of biological membranes. Beyond a certain reversible or repairable threshold, damage to membranes, especially to endothelial cell membranes, can lead to local vascular thrombosis and shutdown of blood circulation.

In using PDT in the present invention, the patient is first given an injection or infusion of a photosensitizing carborane-containing porphyrin of formula (1). Fiber-optic probes are then used to illuminate the tumor tissue. For malignant tumors, it is preferable that the PDT photosensitizers have optical absorbance peaks at sufficiently long wavelengths for maximum penetration to the depth of the tumor.

In a preferred embodiment, the therapeutic treatment of malignant tumors is augmented by the use of SPECT or PET. In SPECT, the patient is first given an infusion or injection of a compound of formula (1) wherein M is a gamma-emitting radioactive metal ion. The patient's head is then scanned noninvasively and the radionuclide concentration, and hence indirectly, the average boron concentration, in each pixel or voxel representing brain or brain tumor tissue is imaged. Contour lines representing zones of equal boron-10 concentration can thereby be drawn on each image of the brain.

SPECT of the brain is at least one order of magnitude more sensitive to isotopic tracers than is conventional radiography or computerized tomography. In addition, SPECT results, as opposed to results from conventional radiography, can be analyzed to provide quantitative information either in defined volumes or voxels of the brain images, in the concentrations of boron relevant to BNCT treatment planning and implementation. SPECT scanning can indicate the presence of a tumor in the patient, as well as its location in the brain or elsewhere in the body. SPECT scanning is noninvasive, fast, and convenient.

However, the positron emitting PET-imageable radioisotope Cu-64, is more readily available than is Cu-67, used in SPECT. Because of the much greater availability of Cu-64, we have carried out preclinical PET studies using a Cu-64 labeled porphyrin.

In another preferred embodiment, the therapeutic treatment of malignant tumors is augmented by the use of MRI. In MRI, a patient is first given an infusion or injection of a solution containing a carborane-containing porphyrin of formula (I) chelated to a suitable paramagnetic metal ion. For a brain tumor, the patient's head is then scanned and the paramagnetic metal ion concentration, and thus, boron concentration in the brain is imaged and quantified. MRI utilizing the compounds of the present invention may permit rapid enhanced targeting and treatment planning for neutron irradiation in BNCT before, during and after infusion when the boronated compound is being redistributed in blood, tumor, and healthy tissue.

The carborane-containing porphyrins of the present invention are synthesized through a series of separate steps. Provided below is first, a summary of the synthetic steps required for the preparation of the preferred carborane-containing porphyrins of the present invention, wherein $Y^1$, $Y^2$, $Y^3$, and $Y^4$ are represented by the formula

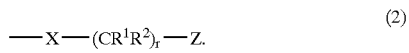

(2)

The synthetic summary provides general methods for synthesizing compounds of the invention, and thereby includes several different specific ways to achieve any one synthesis. For example, different starting materials may be used to synthesize the same product, and each starting material may require a different set of reaction conditions such as temperature, reaction time, solvents, and extraction and purification procedures.

The specific examples describe a preferred method for synthesizing the compounds of the present invention. The scope of this invention is not to be in any way limited by the examples set forth herein. For example, assymetric carborane-containing tetraphenylporphyrin compounds can be synthesized by using a mixture of different benzaldehyde or dibenzaldehyde starting materials and proceeding with a similar synthetic reaction as shown in reaction scheme 6.

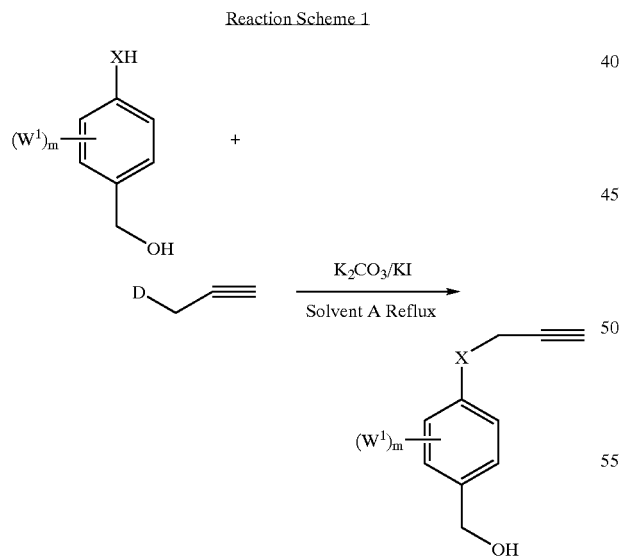

Reaction Scheme 1 where X is either O or S, D is a halogen, solvent A is preferably a polar non-protic solvent such as acetone; $W^1$ is hydroxy, alkoxy, —C(O)$OR^5$, —$SOR^6$, —$SO_2R^6$, nitro, amido, ureido, carbamato, —$SR^7$, —$NR^8R^9$, poly-alkyleneoxide, wherein $R^5$, $R^6$, $R^7$, $R^8$, and $R^9$ are independently selected from hydrogen and $C_1$ to $C_4$ alkyl; and m is 0 or an integer from 1 to 4.

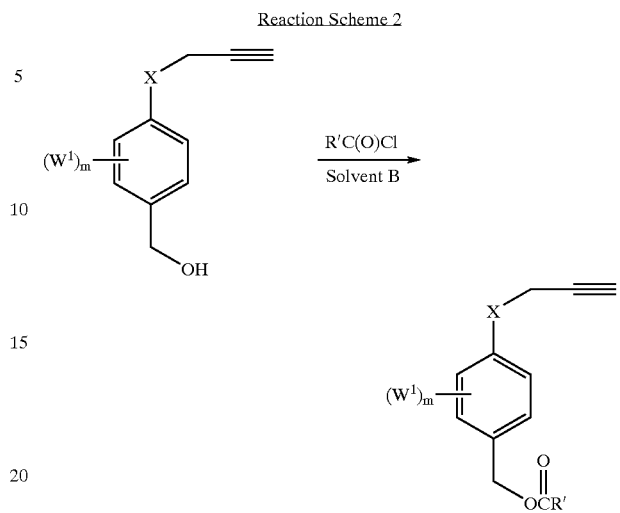

Reaction Scheme 2 where X, $W^1$, and m are as defined above, solvent B is preferably a proton scavenger such as pyridine, and R is an alkyl, cycloalkyl or aryl group.

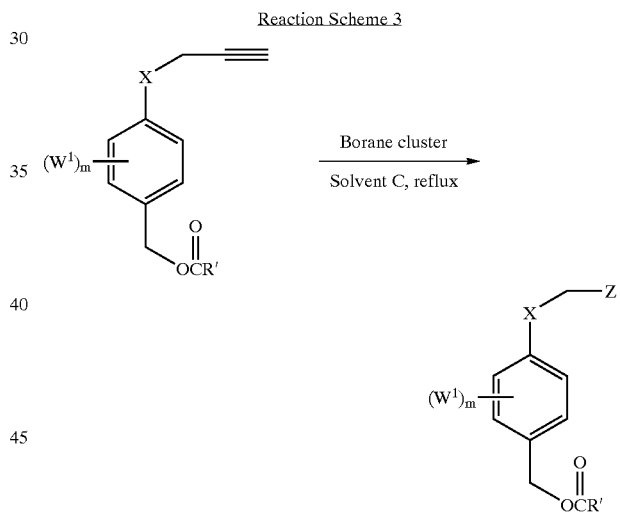

Reaction Scheme 3 where X, $W^1$, m, and R' are as defined previously, and solvent C is preferably a higher boiling hydrocarbon such as toluene. The borane cluster is any cluster comprising at least three boron atoms, or at least one carbon atom and at least five boron atoms, within a cage structure. For example, the borane cluster can be decaborane, $B_{10}H_{14}$. The borane cluster reacts with the triple bond of the propargyl starting material to form the carboranyl product. Thus, in the case of decaborane, Z represents the carborane —$C_2HB_{10}H_{10}$. Z represents any carborane cluster comprising at least two carbon atoms and at least three boron atoms, or at least one carbon atom and at least five boron atoms, within a cage structure. For example, the carborane cluster may be —$C_2HB_9H_{10}$ or —$C_2HB_{10}H_{10}$, wherein —$C_2HB_9H_{10}$ is nido ortho-, meta-, or para-carborane, and —$C_2HB_{10}H_{10}$ is closo ortho-, meta-, or para-carborane.

Reaction Scheme 4

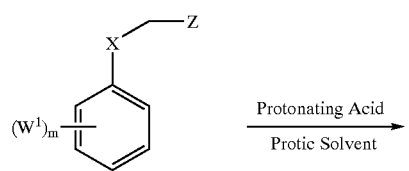

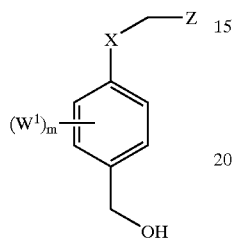

where X, W¹, m, R', and Z are as defined previously. The protonating acid is any acid, acid mixture, or sequence of acid additions capable of converting the ester into the alcohol product. Preferably, the protonating acid is concentrated HCl. The protic solvent may be, for example, an alcohol such as methanol.

Reaction Scheme 5

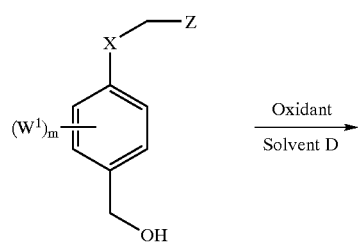

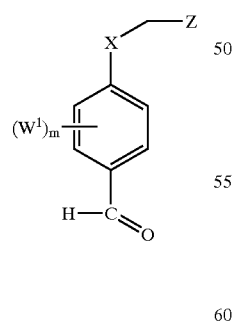

where X, W¹, m, and Z are as defined previously, solvent D is a polar non-protic solvent, preferably dichloromethane, and the oxidant is any oxidizing compound capable of selectively converting a primary alcohol to an aldehyde, preferably 2,3-dichloro-5,6-dicyano-1,4-benzoquinone (DDQ) or pyridinium chlorochromate (PCC).

Reaction Scheme 6

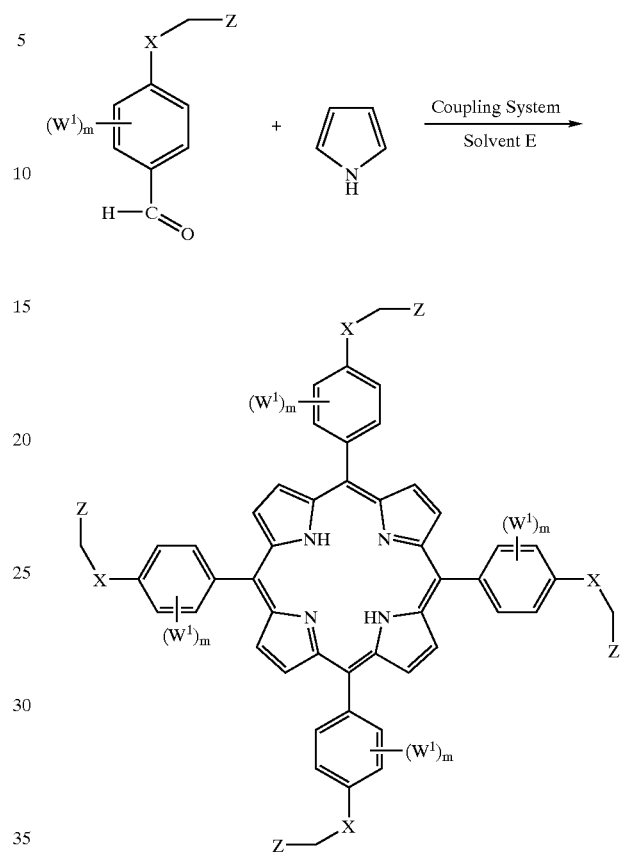

where X, W¹, m, and Z are as defined previously. The coupling system preferably comprises a Lewis acid (electron acceptor) such as boron trifluoride ($BF_3$) or trifluoroacetic acid (TFA) to form the intermediate porphyrinogen from the pyrrole and benzaldehyde and an oxidizing agent such as 2,3-dichloro-5,6-dicyano-1,4-benzoquinone (DDQ) to oxidize the porphyrinogen to porphyrin. Solvent E is a nonpolar non-protic solvent, preferably dichloromethane.

Reaction Scheme 7

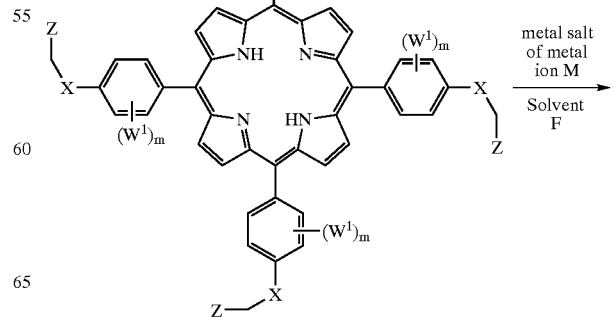

-continued

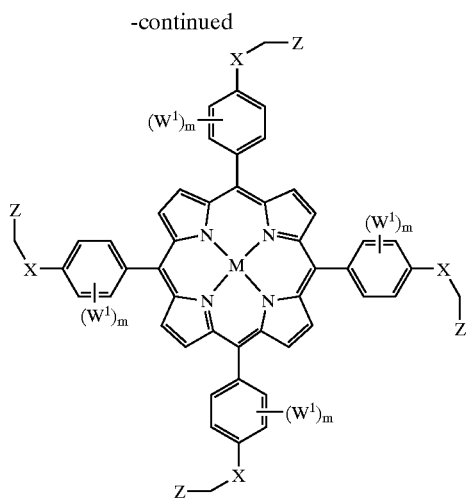

where X, W¹, m, and Z are as defined previously. In a preferred embodiment, M is selected from the group consisting of vanadium (V), manganese (Mn), iron (Fe), ruthenium (Ru), technetium (Tc), chromium (Cr), platinum (Pt), cobalt (Co), nickel (Ni), copper (Cu), zinc (Zn), germanium (Ge), indium (In), tin (Sn), yttrium (Y), gold (Au), barium (Ba), tungsten (W), and gadolinium (Gd). In a more preferred embodiment, M is copper (Cu) or nickel (Ni). The metal salt used contains the metal ion M chelated to the porphyrin. For example, for the compound where M is desired to be copper, copper acetate, i.e., $Cu(OAc)_2 \cdot H_2O$, may be used as the metal salt. Solvent F is any solvent or solvent mixture capable of at least partially solubilizing the porphyrin and metal salt, and that does not interfere with incorporating the metal into the porphyrin.

EXAMPLES

Examples have been set forth below for the purpose of illustration and to describe the best mode of the invention at the present time. The scope of the invention is not to be in any way limited by the examples set forth herein.

Example 1

Synthesis of 3-methoxy-4-propargyloxybenzylalcohol (I)

Finely powdered $K_2CO_3$, 10.4 grams (0.075 moles), and KI, 9.1 grams (0.060 moles), were placed in a 300 mL round-bottomed flask equipped with a magnetic stir bar, and 150 mL acetone was added. 3-methoxy-4-hydroxybenzyl alcohol, 7.71 grams (0.050 moles), and propargyl chloride, 4.10 grams (0.055 moles), were then added, and the mixture stirred and refluxed for approximately 48 hours. The results from thin layer chromatography showed no starting material (3-methoxy-4-hydroxybenzyl alcohol) as well as the presence of a new compound. The solution was then filtered. The acetone of the resulting filtrate was removed by rotary evaporation, leaving an oily residue. The oily residue was dissolved in 50 mL dichloromethane and washed with water (30 mL×2) and then dried over anhydrous potassium carbonate. After filtering the organic phase, the solvents were removed by rotary evaporation, leaving a liquid product. 9 grams of product was obtained, which corresponds to a 94% yield.

The product gave the following proton nuclear magnetic resonance (¹H NMR) spectrum in ppm (in $CDCl_3$ solvent): 2.49 (triplet, 1H, alkynyl); 2.57 (singlet, 1H, hydroxyl); 3.81 (singlet, 3H, methyl); 4.55 (doublet, 2H, methylene); 6.83 (multiplet, 1H, aryl); 6.89 (multiplet, 1H, aryl); 6.94 (multiplet, 1H, aryl). The product gave the following proton-decoupled carbon-13 nuclear magnetic resonance (¹³C NMR) spectrum in ppm (in $CDCl_3$ solvent): 55.8 (methylene); 56.8 (methyl); 64.8 (methylene); 75.8 (alkynyl); 78.5 (alkynyl); 110.2 (aryl); 114.3 (aryl); 119.0 (aryl); 135.2 (aryl); 146.0 (aryl); 149.7 (aryl). The mass spectrum (FAB) showed a parent ion peak of 192.1 that matched the molecular weight of the compound.

Example 2

Synthesis of 3-methoxy-4-propargyloxybenzyl acetate (II)

Acetyl chloride, 1.38 grams (0.0176 moles), was dissolved in 10 mL of pyridine in a 100 mL round flask cooled in an ice bath. A solution of 3-methoxy-4-propargyloxybenzylalcohol (I), made by dissolving 2.82 grams (0.0146 moles) of (I) in 15 mL pyridine, was added dropwise into the flask. The mixture was stirred for five hours, after which time the solvent was removed by rotary evaporation. The resulting residue was cooled to room temperature, and then dissolved in dichloromethane (30 mL). The organic phase was washed with aqueous 3N HCl and then water and dried over anhydrous magnesium sulfate. After filtering, the solvent of the organic phase was removed by rotary evaporation, leaving a yellow oil, which solidified upon standing. Recrystallization in methanol yielded 2.91 grams of the white crystalline solid, which corresponds to an 85% yield.

The product had a melting point of 69–71° C. and gave the following ¹H NMR spectrum in ppm (in $CDCl_3$ solvent): 2.09 (singlet, 3H, methyl); 2.50 (triplet, 1H, alkynyl); 3.89 (singlet, 3H, methyl); 4.76 (doublet, 2H, methylene); 5.05 (singlet, 2H, methylene); 6.92 (singlet, 1H, aryl); 6.93 (multiplet, 1H, aryl); 7.01 (doublet, 1H, aryl). The product gave the following proton-decoupled carbon-13 nuclear magnetic resonance (¹³C NMR) spectrum in ppm (in $CDCl_3$ solvent): 21.2 (methyl); 56.1 (methyl); 56.9 (methylene); 66.6 (methylene); 76.0 (alkynyl); 78.5 (alkynyl); 112.4 (aryl); 114.3 (aryl); 121.1 (aryl); 130.0 (aryl); 147.0 (aryl); 149.8 (aryl); 171.0 (carbonyl). The mass spectrum (FAB) showed a parent ion peak of 234.6 that matched the molecular weight of the compound.

Example 3

Synthesis of 3-methoxy-4-o-oxymethylcarboranylbenzyl acetate (III)

Decaborane, 2.07 grams (0.017 moles), was stirred in 100 mL of toluene in a 250 mL round-bottomed flask at room temperature under an argon atmosphere. Acetonitrile, 2.1 mL (0.040 moles), was added by syringe. The mixture was allowed to stir for three hours. 3-methoxy-4-propargyloxy-benzyl acetate (II), 3.82 grams (0.0163 moles), was then added, and the mixture slowly heated to 80–90° C. The mixture was maintained at a temperature of 80–90° C. under an argon atmosphere for three days, after which time the results from thin layer chromatography showed the no presence of starting material (II) as well as the presence of a new compound. The solvents from the mixture were then removed by rotary evaporation. The resulting residue was dissolved in 50 mL of dichloromethane, which was washed with 20 mL of 10% sodium bicarbonate and then twice with water (20 mL each), and then dried over anhydrous sodium sulfate. After filtering the organic phase, the solvent was removed by rotary evaporation, leaving a yellow oil which crystallized upon standing. 4.64 grams of product was obtained, which corresponds to an 80% yield.

The product had a melting point of 84–85° C. and gave the $^1$H NMR spectrum in ppm (in CDCl$_3$ solvent): 2.00 (singlet, 3H, CH$_3$); 3.76 (singlet, 3H, OCH$_3$); 4.29 (singlet, 1H, CH); 4.54 (singlet, 2H, CH$_2$CCHB$_{10}$H$_{10}$); 4.95 (singlet, 2H, ArCH$_2$); 6.74 (multiplet, 2H, ArH); 7.17 (singlet, 1H, ArH). The product gave the following proton-decoupled $^{13}$C NMR spectrum in ppm (in CDCl$_3$ solvent): 21.1 (OCH$_3$); 56.0 (ArOCH$_2$); 58.0 (OCH$_3$); 66.4 (ArCH$_2$); 71.6 (—CCHB$_{10}$H$_{10}$); 72.1 (—CCHB$_{10}$H$_{10}$); 112.8 (aryl); 116.8 (aryl); 121.2 (aryl); 132.0 (aryl); 146.8 (aryl); 150.4 (aryl); 171.0 (CO). The mass spectrum (FAB) showed a parent ion peak of 352.8 that matched the molecular weight of the compound.

Example 4

Synthesis of 3-methoxy-4-o-oxymethylcarboranylbenzyl alcohol (IV)

Concentrated hydrochloric acid, 2 mL, was added to a solution composed of 4 grams (11 millimoles) of 3-methoxy-4-o-oxymethylcarboranylbenzyl acetate (III) in 50 mL methanol. The mixture was refluxed for three hours, after which time the results from thin layer chromatography showed no presence of starting material (III) and the presence of a new compound. The solvents were then removed by rotary evaporation, leaving a gold-colored oil. On standing at room temperature, the oil solidified to a semisolid. 3.50 grams of product was obtained, which corresponds to a 99% yield.

The product gave the following proton nuclear magnetic resonance ($^1$H NMR) spectrum in ppm (in CDCl$_3$ solvent): 3.39 (singlet, 3H, OCH$_3$); 3.85 (singlet, 2H, ArCH$_2$); 4.33 (singlet, 1H, CH); 4.39 (singlet, 2H, CH$_2$CCHB$_{10}$H$_{10}$); 6.85 (multiplet, 2H, ArH); 6.92 (multiplet, 1H, ArH). The product gave the following proton-decoupled $^{13}$C NMR spectrum in ppm (in CDCl$_3$ solvent): 55.9 (ArOCH$_3$); 58.0 (OCH$_3$); 58.3 (ArCH$_2$); 71.7 (—CCHB$_{10}$H$_{10}$); 74.4 (—CCHB$_{10}$H$_{10}$); 112.0 (aryl); 117.0 (aryl); 120.3 (aryl); 134.5 (aryl); 146.4 (aryl); 150.5 (aryl).

Example 5

Synthesis of 3-methoxy-4-o-oxymethylcarboranylbenzaldehyde (V)

Method 1: Pyridinium chlorochromate (PCC), 2.3 grams (11 millimoles), was stirred in 25 mL dichloromethane in a flask submerged in an ice bath. A solution of the 1.71 grams (5.5 millimoles) 3-methoxy-4-o-oxymethylcarboranyl benzyl alcohol (IV) dissolved in 25 mL dichloromethane was added dropwise to the cooled PCC solution. The resulting mixture was stirred for two hours, after which time thin layer chromatography showed no presence of starting material (IV) as well as the presence of a new compound. The resulting black heterogeneous solution was filtered through a sintered glass funnel containing silica (2 cm). The silica was washed thoroughly with additional dichloromethane to extract the product. The solvents were removed from the filtrate by rotary evaporation, leaving an oily residue, which solidified upon standing. 1.6 grams of product was obtained, which corresponds to a 94% yield.

Method 2: Equimolar amounts of (IV) and 2,3-dichloro-5,6-dicyano-1,4-benzoquinone (DDQ) were stirred in dioxane for 1 hour. The solvent was then removed by rotary evaporation. Dichloromethane was then added to selectively extract the product. The insoluble DDQH$_2$ side-product was removed by filtration. Rotary evaporation of the resulting filtrate yielded the final product.

The product had a melting point of 146–147° C. and gave the following $^1$H NMR spectrum in ppm (in CDCl$_3$ solvent): 3.92 (singlet, 3H, OCH$_3$); 4.28 (singlet, 1H, CH); 4.51 (singlet, 2H, CH$_2$CCHB$_{10}$H$_{10}$); 6.92 (singlet, 1H, ArH); 7.44 (multiplet, 2H, ArH); 9.88 (singlet, 1H, CHO). The product gave the following proton-decoupled carbon-13 nuclear magnetic resonance ($^{13}$C NMR) spectrum in ppm (in CDCl$_3$ solvent): 56.2 (ArOCH$_2$); 58.1 (OCH$_3$); 70.6 (—CCHB$_{10}$H$_{10}$); 71.4 (—CCHB$_{10}$H$_{10}$); 110.3 (aryl); 114.4 (aryl); 126.0 (aryl); 132.3 (aryl); 150.6 (aryl); 190.9 (CO). The mass spectrum (FAB) showed a parent ion peak of 309.7 that matched the molecular weight of the compound.

Example 6

Synthesis of meso-5, 10, 15, 20-tetrakis[3-methoxy-4-o-oxymethylcarboranylphenyl] porphyrin (VI)

3-methoxy-4-o-oxymethylcarboranylbenzaldehyde (V), 50 milligrams (0.136 millimoles), was placed in a dry 100 mL round-bottomed flask and stoppered with a rubber septum. A solution of freshly distilled pyrrole, 9.5 microliters (0.136 millimoles) of pyrrole in 40 mL of dichloromethane, was transferred by syringe to the flask containing (V). The resulting mixture was deoxygenated by bubbling argon directly into the solution (with an outlet needle in septum) while stirring for 15 to 20 minutes. Trifluoroacetic acid (TFA), 5.4 microliters (0.045 millimoles), was added to the mixture using a microliter syringe. The mixture was allowed to stir under an argon atmosphere overnight. DDQ, 34 milligrams (0.149 millimoles), was then added, which immediately turned the solution very dark. The solution was refluxed for one hour. The solution was then purified using a 30 mL sintered glass funnel containing about 20 mL silica. The resulting dark filtrate was rotary evaporated to dryness. The results from thin layer chromatography confirmed the presence of the porphyrin product as well as some contaminants. The solid was redissolved in dichloromethane and then further purified using another short column of silica eluting with a 1:1 solvent mixture of dichloromethane to hexanes. The results from thin layer chromatography confirmed the absence of the contaminants. The resulting dark filtrate was rotary evaporated to dryness, resulting in 15 milligram, of product, which corresponds to a 31% yield.

The product gave the following proton nuclear magnetic resonance ($^1$H NMR) spectrum in ppm (in $CDCl_3$ solvent): −2.77 (singlet, 2H, NH); 3.94 (singlet, 12H, $OCH_3$); 4.50 (singlet, 4H, CH); 4.74 (singlet, 8H, $CH_2CCHB_{10}H_{10}$); 7.21 (doublet, 4H, ArH); 7.72 (doublet, 4H, ArH); 7.77 (singlet, 4H, ArH); 8.85 (singlet, 8H, pyrrole-H). The mass spectrum (FAB) showed a parent ion peak of 1424.7 that matched the molecular weight of the compound. The ultraviolet-visible absorbance spectrum of the product in dichloromethane showed the following peaks in nanometers of wavelength: 423, 517, 554, 593, and 648.

Example 7

Synthesis of copper meso-5, 10, 15, 20-tetrakis[3-methoxy-4-o-oxymethylcarboranyl phenyl]porphyrin, (VII)

A solution of $Cu(OAc)_2.H_2O$ (20 milligrams, 100 millimoles) in 5 mL methanol was added into a solution of porphyrin compound (VI) (130 milligrams, 91 millimoles) in 10 mL dichloromethane. The mixture was stirred for 20 minutes. The solvent was then removed by rotary evaporation. The resulting residue was dissolved in dichloromethane, washed with water and then dried over anhydrous sodium sulfate. The drying agent was filtered off. The solvent of the filtrate was removed by rotary evaporation, leaving a red solid residue. The solid was re-dissolved in dichloromethane and purified using a silica pad eluting with a 1:1 solvent mixture of hexane and dichloromethane. The solvents were removed by rotary evaporation, leaving the red copper porphyrin compound, 132 milligrams, which corresponds to 98% yield.

The mass spectrum (FAB) showed a parent ion peak of 1486.3 that matched the molecular weight of the compound. The ultraviolet-visible absorbance spectrum of the product showed the following peaks in nanometers of wavelength (in dichloromethane solvent): 418, 542.

Example 8

Synthesis of meso-5, 10, 15, 20-tetrakis[3-hydroxy-4-o-oxymethylcarboranylphenyl] porphyrin (VIII)

Porphyrin compound (VI), 44 milligrams (0.03 millimoles), was placed in a dry 50 mL flask under an atmosphere of argon and the flask sealed with a rubber septum. Dry dichloromethane, 15 mL, was added by syringe to dissolve the porphyrin compound (VI). Boron tribromide, 1 mL of a 1M solution in dichloromethane (1.0 millimoles), was transferred by syringe to the solution containing the porphyrin compound (VI). The reaction mixture was stirred at room temperature for 30 minutes. Excess boron tribromide was destroyed by adding approximately 10 mL of dilute 10% aqueous sodium bicarbonate solution. The solution was stirred for 30 minutes, and then neutralized with enough dilute HCl to adjust the pH to approximately 6. The organic phase was separated from the aqueous phase, washed with 10% aqueous sodium bicarbonate, and then dried over anhydrous sodium sulfate. The resulting green solution was purified using a silica pad and eluted with a 5:1 acetone to methanol solvent mixture. The solvent was removed by rotary evaporation, leaving a reddish brown solid. The reddish brown solid was found to be more soluble in polar organic solvents such as methanol and acetone than in dichloromethane and chloroform. 38 milligrams of the product was obtained, corresponding to a 91% yield.

The product gave the following proton nuclear magnetic resonance ($^1$H NMR) spectrum in ppm (in $CDCl_3$ solvent): −2.88 (singlet, 2H, NH); 4.04 (singlet, 4H, CH); 4.71 (singlet, 8H, $CH_2CCHB_{10}H_{10}$); 5.64 (singlet, 4H, ArOH); 7.10 (singlet, 4H, ArH); 7.63 (singlet, 4H, ArH); 7.77 (singlet, 4H, ArH); 8.82 (singlet, 8H, pyrrole-H). The mass spectrum (FAB) showed a parent ion peak of 1368.0 that matched the molecular weight of the compound. The ultraviolet-visible absorbance spectrum of the product showed the following peaks in nanometers of wavelength (in acetone solvent): 420, 513, 549, 591, 648.

Example 9

Synthesis of copper meso-5, 10, 15, 20-tetrakis[3-hydroxy-4-o-oxymethylcarboranyl phenyl]porphyrin (IX)

A 1:1.1 molar solution of porphyrin compound (VIII) (50 milligrams, 36.5 millimoles) to $Cu(OAc)_2.H_2O$ (8 milligrams, 40 millimoles) to $Cu(OAc)_2H_2O$ was prepared by dissolving the two compounds in methanol. The resulting purple solution was stirred for 20 minutes during which time the color turned to red. The solvent was then removed by rotary evaporation. The resulting residue was dissolved in dichloromethane to make an organic phase, which was washed with water and then dried over anhydrous sodium sulfate. The solvent of the organic phase was removed by rotary evaporation, leaving a red copper porphyrin compound. The compound was re-dissolved in dichloromethane and purified on a silica pad eluting with a 3:1:1 solvent mixture of hexane to dichloromethane to acetone. The solvent of the organic phase was removed by rotary evaporation, leaving 36 milligrams of the copper porphyrin compound (IX) (70% yield).

The mass spectrum (FAB) showed a parent ion peak of 1428.0 that matched the molecular weight of the compound. The ultraviolet-visible absorbance spectrum of the product showed the following peaks in nanometers of wavelength (in acetone): 417, 534.

Example 10

Preparation of Boronated Porphyrin Solutions

Porphyrin compound (VII) was emulsified in 9% Cremophor EL and 18% propylene glycol in saline (0.9% sodium chloride). Porphyrin compound (IX) was emulsified in 3% Cremophor and 6% propylene glycol in saline.

To prepare a solution of ~3.3 mg/mL porphyrin in 9% Cremophor EL (CRM) and 18% propylene glycol (PRG), the porphyrin was dissolved in tetrahydrofuran (THF) (1.5% of the total volume) and then heated to 40° C. for 15 min. CRM (9% of total volume) was then added and the mixture was heated to 60° C. for 2 hours, which removed most of the THF. After cooling to room temperature, PRG (18% of total volume) was added, followed by slow dropwise addition of saline (71.5% of total volume) with rapid stirring. The solution was degassed by stirring under vacuum (~30 mm Hg) for 30–60 min and then filtered (Millipore, 8 $\mu$m).

The preparation of the 3% CRM/6% PRG solution follows the same protocol as above, except that 3% CRM (3% of total volume) and 6% PRG (6% of total volume) is used.

Example 11

Biodistribution of Porphyrin VII in Mice Bearing EMT-6 Carcinomas

BALB/c mice bearing subcutaneously implanted EMT-6 mammary carcinomas implanted on the dorsal thorax were given a total dose of 110 or 185 milligrams porphyrin compound (VII) per kilogram body weight (32 or 54 mg B/kg, respectively). At two and four days after the last injection, mice were euthanized, and tumor, blood, brain, and liver were removed for boron analyses. The blood was first analyzed for hematologic parameters that indicate toxicity before it was analyzed for boron. Tables 1 and 2 below show the average boron concentrations for different types of tissue from BALB/c mice (5/time-point).

Table 1

Average boron concentrations ($\mu$g/g wet tissue) in various tissues in mice (n=5) given 110 mg/kg porphyrin VII (32 mg B/kg) in 3 i.p. injections over a period of 8 hours.

| Time after last injection | EMT-6 Tumor $\mu$g/g | Blood $\mu$g/g | Brain $\mu$g/g | Liver $\mu$g/g |
|---|---|---|---|---|
| 2 days | 80.4 ± 18.8 | 5.5 ± 3.5 | 0.2 ± 0.1 | 301 ± 19.2 |
| 4 days | 69.3 ± 78.5 | 0.4 ± 0.2 | 0.1 ± 0.0 | 254 ± 63.8 |

Table 2

Average boron concentrations ($\mu$g/g wet tissue) in various tissues in mice (n=5) given 185 mg/kg porphyrin VII (54 mg B/kg) in 6 i.p. injections over a period of 32 hours.

| Time after last injection | EMT-6 Tumor $\mu$g/g | Blood $\mu$g/g | Brain $\mu$g/g | Liver $\mu$g/g |
|---|---|---|---|---|
| 2 days | 191 ± 66.7 | 0.9 ± 1.1 | 0.1 ± 0.1 | 592 ± 153 |
| 4 days | 167 ± 51.9 | 0.1 ± 0.0 | 0.0 ± 0.2 | 433 ± 49.2 |

The boron concentrations in tumors were extremely high considering the relatively low boron-injected dose. The resulting % injected dose of ~12% is the highest ever observed in the EMT-6 carcinoma in our laboratory. As with other lipophilic tetraphenylporphyrins, the boron in blood and in brain were negligible by 2 days after the last injection yielding very high tumor-blood and tumor-brain boron ratios.

Example 12

Weight Changes and Hematologic Parameters from Porphyrin VII

Table 3

Weight changes and hematologic parameters in mice given 110 mg/kg porphyrin VII (32 mg B/kg) or solvent only (9% Cremophor and 18% propylene glycol in saline) at 2 or 4 days after the last injection. Values are reported as median (and range).

TABLE 3

Weight changes and hematologic parameters in mice given 110 mg/kg porphyrin VII (32 mg B/kg) or solvent only (9% Cremophor and 18% propylene glycol in saline) at 2 or 4 days after the last injection. Values are reported as median (and range).

| Compound | Time after last injection | Number of mice | % Weight change | Platelets ($10^3$/mm$^3$) | Lymphocytes (% WBC) | Granulocytes (% WBC) |
|---|---|---|---|---|---|---|
| Porphyrin VII | 2 days | 10 | −3.6 (−7.8–0.5) | 85 (48–100) | 41 (35–65) | 55 (33–63) |
| Solvent only | 2 days | 4 | −1.3 (−4.5–1.1) | 640 (568–730) | 68 (61–71) | 28 (26–32) |
| Porphyrin VII | 4 days | 5 | −4.6 (−16—0.5) | 507 (394–652) | 48 (40–51) | 49 (45–57) |
| Solvent only | 4 days | 4 | −0.7 (−2.2–2.1) | 527 (500–618) | 71 (70–72) | 26 (24–26) |

Table 4

Weight changes and hematologic parameters in mice given 185 mg/kg porphyrin VII (54 mg B/kg) or solvent only (9% Cremophor and 18% propylene glycol in saline) at 2 or 4 days after the last injection. Values are reported as median (and range).

TABLE 4

Weight changes and hematologic parameters in mice given 185 mg/kg porphyrin VII (54 mg B/kg) or solvent only (9% Cremophor and 18% propylene glycol in saline) at 2 or 4 days after the last injection. Values are reported as median (and range).

| Compound | Time after last injection | Number of mice | % Weight change | Platelets ($10^3/mm^3$) | Lymphocytes (% WBC) | Granulocytes (% WBC) |
|---|---|---|---|---|---|---|
| Porphyrin VII | 2 days | 10 | −4.7 (−9.3–0.9) | 181 (105–248) | 35 (30–58) | 62 (38–67) |
| Solvent only | 2 days | 4 | −1.3 (−4.5–1.1) | 640 (568–730) | 68 (61–71) | 28 (26–32) |
| Porphyrin VII | 4 days | 5 | 5.2 (1.5–7.4) | 429 (346–481) | 57 (51–62) | 40 (34–46) |
| Solvent only | 4 days | 4 | −0.7 (−2.2–2.1) | 527 (500–618) | 71 (70–72) | 26 (24–26) |

No visible toxic effects were noted either physically or behaviorally in the mice during and after porphyrin administration. At necropsy, all tissues appeared normal. Tables 3 and 4 show the weight changes and hematologic parameters in BALB/c mice described in Example 11 given 110 or 185 milligrams porphyrin compound VII in 9% Cremophor and 18% propylene glycol in saline per kilogram body weight and comparisons to control mice given solvent only. Weight loss was more significant in mice given porphyrin VII at both doses than in controls and was greater at the higher porphyrin dose. Decreased platelet count (thrombocytopenia) was also more prevalent in mice given porphyrin VII than in controls. The counts were surprisingly closer to those of controls at the higher porphyrin dose. Both weight loss and decreased platelets were less pronounced at the 4-day time-point, indicating that the small, but significant deviations are reversible.

Example 13

Biodistribution of Porphyrin IX in Mice Bearing EMT-6 Carcinomas

BALB/c mice bearing subcutaneously implanted EMT-6 mammary carcinomas implanted on the dorsal thorax were given a total dose of 118 milligrams porphyrin compound (IX) per kilogram body weight (36 mg B/kg, respectively). At two and four days after the last injection, mice were euthanized, and tumor, blood, brain, and liver were removed for boron analyses. The blood was first analyzed for hematologic parameters that indicate toxicity before it was analyzed for boron. Table 5 shows the average boron concentrations for different types of tissue from BALB/c mice (5/time-point).

Table 5

Average boron concentrations in various tissues in mice given 118 mg/kg porphyrin IX (36 mg B/kg).

| Time after last injection | EMT-6 Tumor $\mu g/g$ | Blood $\mu g/g$ | Brain $\mu g/g$ | Liver $\mu g/g$ |
|---|---|---|---|---|
| 2 days | 35.3 ± 4.8 | 0.3 ± 0.1 | 0.3 ± 0.2 | 486 ± 50.2 |
| 4 days | 26.7 ± 7.9 | 0.2 ± 0.1 | 0.0 ± 0.1 | 434 ± 64.6 |

Table 6

Weight changes and hematologic parameters in mice given 118 mg/kgporphyrin (IX) (36 mg B/kg) or solvent only (3% Cremophor and 6% propylene glycol in saline). Values are given in both median and (range).

TABLE 6

Weight changes and hematologic parameters in mice given 118 mg/kg porphyrin (IX) (36 mg B/kg) or solvent only (3% Cremophor and 6% propylene glycol in saline). Values are given in both median and (range).

| Compound | Time after last injection | Number of mice | % Weight change | Platelets ($10^3/mm^3$) | Lymphocytes (% WBC) | Granulocytes (% WBC) |
|---|---|---|---|---|---|---|
| Porphyrin IX | 2 days | 10 | −0.1 (−2.0–1.4) | 617 (441–781) | 53 (46–56) | 43 (39–49) |
| Solvent only | 2 days | 4 | −1.3 (−4.5–1.1) | 640 (568–730) | 68 (61–71) | 28 (26–32) |

TABLE 6-continued

Weight changes and hematologic parameters in mice given 118 mg/kg porphyrin (IX) (36 mg B/kg) or solvent only (3% Cremophor and 6% propylene glycol in saline). Values are given in both median and (range).

| Compound | Time after last injection | Number of mice | % Weight change | Platelets ($10^3/mm^3$) | Lymphocytes (% WBC) | Granulocytes (% WBC) |
|---|---|---|---|---|---|---|
| Porphyrin IX | 4 days | 5 | 2.4 (0.9–3.9) | 633 (561–824) | 54 (52–59) | 41 (37–44) |
| Solvent only | 4 days | 4 | −0.7 (−2.2–2.1) | 527 (500–618) | 71 (70–72) | 26 (24–26) |

The results of the preliminary biodistribution study showed that although the average tumor boron concentrations for porphyrin IX are lower than those for porphyrin VII, these values can most likely be considered adequate for therapeutic studies. The microlocalization properties of porphyrin IX are likely to be different from those of porphyrin VII, due to its more polar nature. The tumor-to-blood and tumor-to-brain boron ratios for porphyrin IX are quite high two days after the last injection at greater than 100:1. Hematological and weight data did not show the greater weight loss nor thrombocytopenia that was observed for the methoxy analog, porphyrin VII, when compared to controls given solvent only. Thus, the dose can likely be escalated without significantly increasing toxicity.

Thus, while there have been described the preferred embodiments of the present invention, those skilled in the art will realize that other embodiments can be made without departing from the spirit of the invention, which includes all such further modifications and changes as come within the true scope of the claims set forth herein.

What is claimed is:

1. A compound of the formula

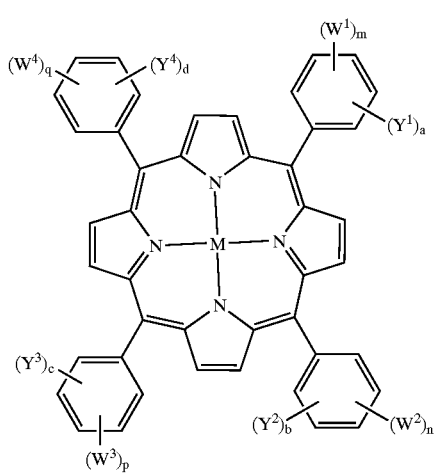

(1)

wherein:

$Y^1$, $Y^2$, $Y^3$, and $Y^4$, are independently on the ortho, meta or para position on the phenyl rings, and are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by the following formula:

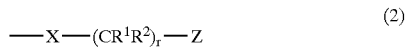

(2)

provided that at least four of $(Y^1)_a$, $(Y^2)_b$, $(Y^3)_c$, and $(Y^4)_d$ are represented by formula (2);

X is oxygen or sulfur;

$R^1$, $R^2$, $R^5$, $R^6$, $R^7$, $R^8$, and $R^9$ are independently selected from hydrogen and $C_1$ to $C_4$ alkyl;

Z is a carborane cluster comprising at least two carbon atoms and at least three boron atoms, or at least one carbon atom and at least five boron atoms, within a cage structure;

r is 0 or an integer from 1 to 20;

$W^1$, $W^1$, $W^3$, and $W^4$ are hydrophilic groups independently selected from hydroxy, alkoxy, —C(O)OR$^5$, —SOR$^6$, —SO$_2$R$^6$, nitro, amido, ureido, carbamato, —SR$^7$, —NR$^8$R$^9$, or polyalkylene oxide;

a, b, c, and d independently represent an integer from 1 to 4;

m, n, p, and q are independently 0 or an integer from 1 to 4;

provided that at least one of m, n, p, and q is not zero, and each of the sums a+m, b+n, c+p, and d+q, independently represents an integer from 1 to 5; and M is either two hydrogen ions; a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein when M is a single monovalent metal ion, the compound is charge-balanced by a counter cation; and when M is a trivalent, tetravalent, pentavalent, or hexavalent metal ion, the compound is charge-balanced by an appropriate number of counter anions, dianions, or trianions.

2. The compound according to claim 1 wherein Z is selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

3. The compound according to claim 1, wherein M is vanadium, manganese, iron, ruthenium, technetium, chromium, platinum, cobalt, nickel, copper, zinc, germanium, indium, tin, yttrium, gold, barium, tungsten, or gadolinium.

4. The compound according to claim 1 wherein a, b, c, and d are 1, and $Y^1$, $Y^2$, $Y^3$, and $Y^4$ are represented by —X—(CR$^1$R$^2$)$_r$—Z (2).

5. The compound according to claim 4 wherein Z is selected from the carboranes —C$_2$HB$_9$H$_{10}$ or —C$_2$HB$_{10}$H$_{10}$, wherein —C$_2$HB$_9$H$_{10}$ is nido ortho-, meta-, or para-carborane, and —C$_2$HB$_{10}$H$_{10}$ is closo ortho-, meta-, or para-carborane.

6. The compound according to claim 5, wherein M is vanadium, manganese, iron, ruthenium, technetium, chromium, platinum, cobalt, nickel, copper, zinc, germanium, indium, tin, yttrium, gold, barium, tungsten, or gadolinium.

7. The compound according to claim 6, wherein X is O; R$^1$ and R$^2$ are H; r is 1; and m, n, p and q are each 1.

8. The compound according to claim 7 wherein $Y^1$, $Y^2$, $Y^3$, and $Y^4$ are in the para position on the phenyl ring, and $W^1$, $W^2$, $W^3$, and $W^4$ are independently, hydroxy or alkoxy groups.

9. The compound according to claim 8 wherein $W^1$, $W^2$, $W^3$, and $W^4$ are alkoxy groups.

10. The compound according to claim 9 wherein the alkoxy groups are methoxy groups.

11. The compound according to claim 10 wherein the methoxy groups are in the meta position of the phenyl ring.

12. A compound according to claim 11, wherein M is either a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein when M is a single monovalent metal ion, the compound is charge-balanced by a counter cation; and when M is a trivalent, tetravalent, pentavalent, or hexavalent metal ion, the compound is charge-balanced by an appropriate number of counter anions, dianions, or trianions.

13. A method of imaging a tumor and surrounding tissue in a subject comprising the administration to the subject of a composition comprising a compound according to claim 12; and observing the metal ion in the subject, thereby imaging the tumor and surrounding tissue.

14. The compound according to claim 8 wherein $W^1$, $W^2$, $W^3$, and $W^4$ are hydroxy groups.

15. The compound according to claim 10 wherein the hydroxy groups are in the meta position of the phenyl ring.

16. A method of bimodal cancer treatment in a subject comprising the administration to the subject of a composition comprising a compound according to claim 15; and the irradiation of said subject.

17. A compound according to claim 15, wherein M is either a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein when M is a single monovalent metal ion, the compound is charge-balanced by a counter cation; and when M is a trivalent, tetravalent, pentavalent, or hexavalent metal ion, the compound is charge-balanced by an appropriate number of counter anions, dianions, or trianions.

18. A method of imaging a tumor and surrounding tissue in a subject comprising the administration to the subject of a composition comprising a compound according to claim 12; and observing the metal ion in the subject, thereby imaging the tumor and surrounding tissue.

19. A method of bimodal cancer treatment in a subject comprising the administration to the subject of a composition comprising a compound according to claim 11; and the irradiation of said subject.

20. A method of bimodal cancer treatment in a subject comprising the administration to the subject of a composition comprising a compound according to claim 1; and the irradiation of said subject.

21. The method according to any of claims 20, 19, or 16 wherein said irradiation is by a method utilizing thermal or epithermal neutrons, or laser red light.

22. The method according to any of claims 20, 19, or 16 wherein said bimodal cancer treatment comprises boron neutron capture therapy (BNCT).

23. The method according to any of claims 20, 19, or 16 wherein said bimodal cancer treatment comprises photodynamic therapy (PDT).

24. The method according to any of claims 20, 19, or 16 wherein said bimodal cancer treatment utilizes single photon emission computed tomography (SPECT) or positron emission tomography (PET) wherein M is a SPECT- and/or PET-imageable radioactive metal ion.

25. The method according to any of claims 20, 19, or 16 wherein said bimodal cancer treatment utilizes magnetic resonance imaging (MRI) wherein M is a paramagnetic metal ion.

26. A compound according to claim 1, wherein M is either a single monovalent metal ion; two monovalent metal ions; a divalent metal ion; a trivalent metal ion; a tetravalent metal ion; a pentavalent metal ion; a hexavalent metal ion; a radioactive metal ion useful in radioisotope-mediated radiation therapy or imageable by single photon emission computed tomography (SPECT) or positron emission tomography (PET); a paramagnetic metal ion detectable by magnetic resonance imaging (MRI); a metal ion suitable for boron neutron capture therapy (BNCT) or photodynamic therapy (PDT); or a combination thereof; wherein when M is a single monovalent metal ion, the compound is charge-balanced by a counter cation; and when M is a trivalent, tetravalent, pentavalent, or hexavalent metal ion, the compound is charge-balanced by an appropriate number of counter anions, dianions, or trianions.

27. A method of imaging a tumor and surrounding tissue in a subject comprising the administration to the subject of a composition comprising a compound according to claim 26; and observing the metal ion in the subject, thereby imaging the tumor and surrounding tissue.

28. The method according to any of claims 27, 18, or 18 wherein said imaging is by a method selected from magnetic resonance imaging (MRI), single photon emission computed tomography (SPECT), or positron emission tomography (PET) methods.

29

29. A compound of the formula

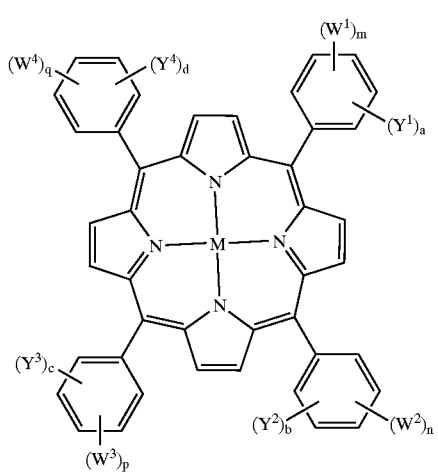

(1)

wherein:

$Y^1$, $Y^2$, $Y^3$, and $Y^4$, are independently on the ortho, meta or para position on the phenyl rings, and are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by the following formula:

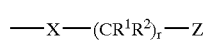

(2)

provided that at least four of $(Y^1)_a$, $(Y^2)_b$, $(Y^3)^c$, and $(Y^4)^d$ are represented by formula (2);

X is oxygen or sulfur;

$R^1$, $R^2$, $R^5$, $R^6$, $R^7$, $R^8$, and $R^9$ are independently selected from hydrogen and $C_1$ to $C_4$ alkyl;

Z is a carborane cluster comprising at least two carbon atoms and at least three boron atoms, or at least one carbon atom and at least five boron atoms, within a cage structure;

r is 0 or an integer from 1 to 20;

$W^1$, $W^2$, $W^3$, and $W^4$ are hydrophilic groups independently selected from hydroxy, alkoxy, —C(O)OR$^5$, —SOR$^6$, —SO$_2$R$^6$, nitro, amido, ureido, carbamato, —SR$^7$, —NR$^8$R$^9$, or polyalkylene oxide;

a, b, c, and d independently represent an integer from 1 to 4;

m, n, p, and q are independently 0 or an integer from 1 to 4;

provided that at least one of m, n, p, and q is not zero, and each of the sums a+m, b+n, c+p, and d+q, independently represents an integer from 1 to 5;

M is a trivalent, tetravalent, pentavalent, or hexavalent metal ion; and wherein the porphyrin-metal complex is charge-balanced by one or more porphyrin compounds containing a divalent negative charge.

30

30. The compound according to claim 29 wherein said one or more porphyrin compounds containing a divalent negative charge are represented by the formula

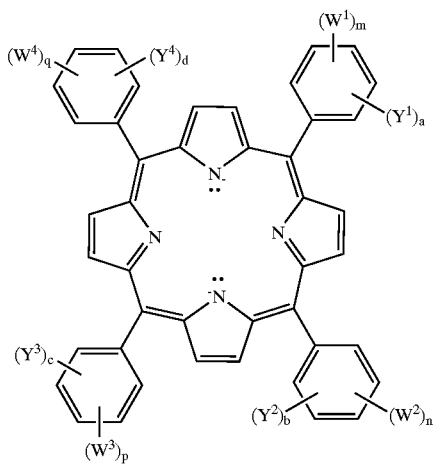

wherein:

$Y^1$, $Y^2$, $Y^3$, and $Y^4$, are independently on the ortho, meta or para position on the phenyl rings, and are independently hydrogen, alkyl, cycloalkyl, aryl, alkylaryl, arylalkyl, heteroaryl, or an alkyl, cycloalkyl, aryl, alkylaryl, arylalkyl, or heteroaryl group substituted with 1 to 4 hydrophilic groups selected from hydroxy, alkoxy, —C(O)OR$^5$, —SOR$^6$, —SO$_2$R$^6$, nitro, amido, ureido, carbamato, —SR$^7$, —NR$^8$R$^9$, or poly-alkyleneoxide; or a substituent represented by the following formula:

(2)

provided that at least four of $(Y^1)_a$, $(Y^2)_b$, $(Y^3)_c$, and $(Y^4)_d$ are represented by formula (2);

X is oxygen or sulfur;

$R^1$, $R^2$, $R^5$, $R^6$, $R^7$, $R^8$, and $R^9$ are independently selected from hydrogen and $C_1$ to $C_4$ alkyl;

Z is a carborane cluster comprising at least two carbon atoms and at least three boron atoms, or at least one carbon atom and at least five boron atoms, within a cage structure;

r is 0 or an integer from 1 to 20;

$W^1$, $W^2$, $W^3$, and $W^4$ are hydrophilic groups independently selected from hydroxy, alkoxy, —C(O)OR$^5$, —SOR$^6$, —SO$_2$R$^6$, nitro, amido, ureido, carbamato, —SR$^7$, —NR$^8$R$^9$, or polyalkylene oxide;

a, b, c, and d independently represent an integer from 1 to 4;

m, n, p, and q are independently 0 or an integer from 1 to 4; and provided that at least one of m, n, p, and q is not zero, and each of the sums a+m, b+n, c+p, and d+q, independently represents an integer from 1 to 5.

* * * * *

UNITED STATES PATENT AND TRADEMARK OFFICE
CERTIFICATE OF CORRECTION

PATENT NO. : 6,995,260 B2
APPLICATION NO. : 10/848741
DATED : February 7, 2006
INVENTOR(S) : Haitao Wu and Michiko Miura It is certified that error appears in the above-identified patent and that said Letters Patent is hereby corrected as shown below:

Column 27: in Claim 12, line 26, delete "A" and insert --The--

Column 28: in Claim 18, line 8, delete "12" and insert --17--

Column 28: in Claim 26, line 40, delete "A" and insert --The--

Column 28: in Claim 28, line 63, delete "claims 27, 18, or 18" and insert --claims 27, 18, or 13--

Signed and Sealed this

Eighteenth Day of March, 2008

JON W. DUDAS
*Director of the United States Patent and Trademark Office*